(12) United States Patent
Leahy et al.

(10) Patent No.: US 9,629,617 B2
(45) Date of Patent: Apr. 25, 2017

(54) ENDOSCOPIC BIOPSY NEEDLE WITH COIL SHEATH

(71) Applicant: Cook Medical Technologies LLC, Bloomington, IN (US)

(72) Inventors: Ronan Leahy, Limerick (IE); Michael S. Clancy, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 164 days.

(21) Appl. No.: 14/195,333

(22) Filed: Mar. 3, 2014

(65) Prior Publication Data
US 2014/0257136 A1 Sep. 11, 2014

Related U.S. Application Data

(63) Continuation of application No. PCT/US2014/013552, filed on Jan. 29, 2014.

(60) Provisional application No. 61/772,831, filed on Mar. 5, 2013, provisional application No. 61/772,831, filed on Mar. 5, 2013.

(51) Int. Cl.
*A61B 10/00* (2006.01)
*A61B 10/04* (2006.01)
*A61B 10/02* (2006.01)

(52) U.S. Cl.
CPC .......... *A61B 10/04* (2013.01); *A61B 10/0275* (2013.01); *A61B 2010/045* (2013.01)

(58) Field of Classification Search
CPC ............ A61B 10/0275; A61B 10/0266; A61B 2010/0208

USPC ......................................................... 600/567
See application file for complete search history.

(56) References Cited

U.S. PATENT DOCUMENTS

| | | | |
|---|---|---|---|
| 4,798,598 A | 1/1989 | Bonello et al. | |
| 5,228,451 A | 7/1993 | Bales et al. | |
| 6,666,847 B2 | 12/2003 | Secrest et al. | |
| 2012/0253228 A1* | 10/2012 | Schembre | A61B 10/0275 600/567 |
| 2013/0006145 A1* | 1/2013 | Toomey | A61B 10/0275 600/567 |
| 2013/0237879 A1* | 9/2013 | Takeuchi | A61B 8/0841 600/567 |

FOREIGN PATENT DOCUMENTS

| | | |
|---|---|---|
| JP | 2008005965 | 1/2008 |
| WO | WO 2012133276 | 10/2012 |

OTHER PUBLICATIONS

English Translation of JP 2008-005965.*

* cited by examiner

*Primary Examiner* — Daniel Cerioni
(74) *Attorney, Agent, or Firm* — Brinks Gilson & Lione

(57) ABSTRACT

A notched tissue-collection needle configured similarly to a fine-needle-aspiration needle is provided with a cutting edge disposed in the notch and configured to excise tissue into the notch for collection. A stylet may be provided through a lumen of the needle during introduction into a patient body. The needle may be provided with echogenicity-enhancing features. A coated-wire sheath through which the needle is slidably disposed includes an overcoating that is thicker along a distal length and thinner along a proximal length.

20 Claims, 3 Drawing Sheets

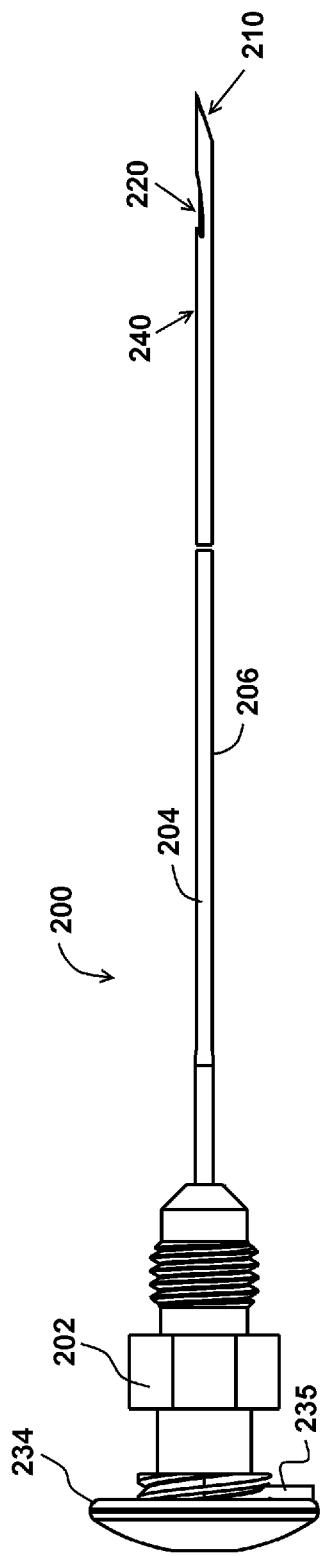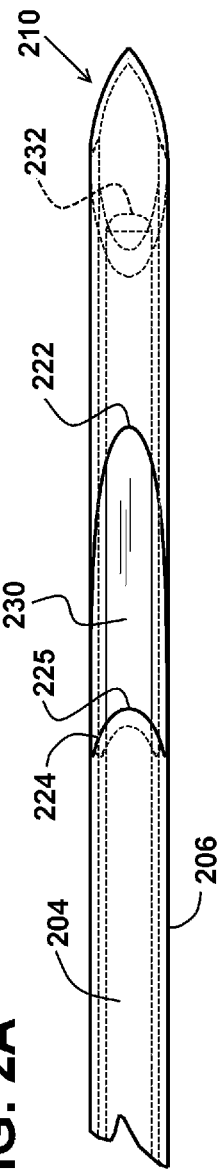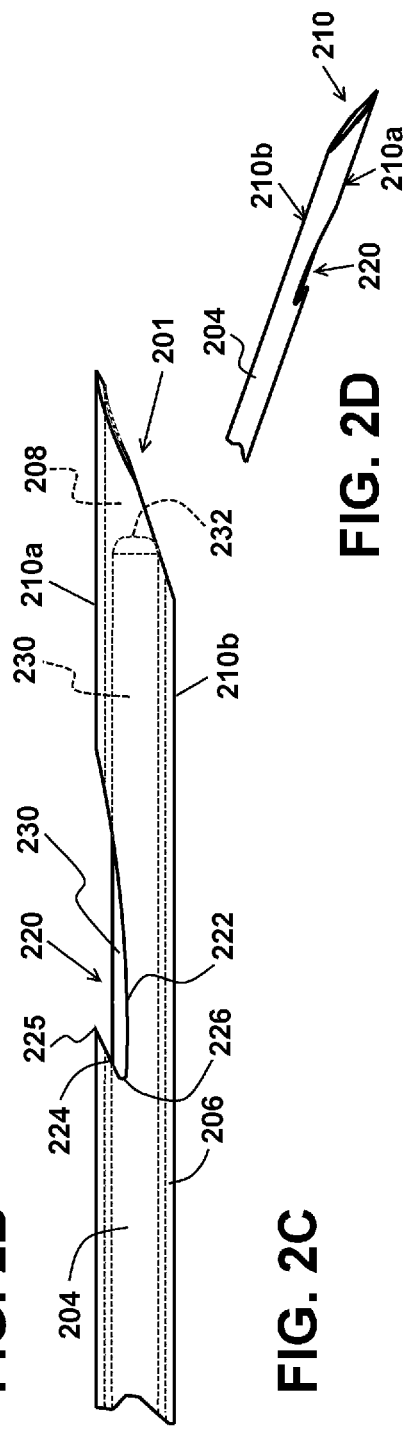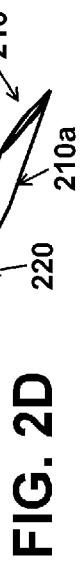
FIG. 2A
FIG. 2B
FIG. 2C
FIG. 2D

ENDOSCOPIC BIOPSY NEEDLE WITH COIL SHEATH

CROSS-REFERENCE TO RELATED APPLICATIONS

This application claims priority to U.S. provisional application Ser. No. 61/772,831, filed Mar. 5, 2013, which is incorporated by reference herein in its entirety.

TECHNICAL FIELD

The invention relates generally to endoscopic surgical devices. More particularly, the invention pertains to a biopsy needle configured for use during minimally-invasive procedures such as endoscopic procedures.

BACKGROUND

Fine needle aspiration (FNA) is a diagnostic biopsy procedure used to obtain a sample from a target site in a patient body. A fine needle (e.g., 19-gauge to 25-gauge) is directed to a target site, and suction is applied to the proximal end of a lumen of the needle to aspirate cells through its distal end. The procedure typically is far less invasive than other biopsy techniques, whether performed percutaneously (e.g., to sample a suspected breast tumor or subcutaneous lesion) or endoscopically (e.g., to sample a suspected cholangiocarcinoma via a duodenoscope). Moreover, advances in endoscopic ultrasound (EUS) technology have helped physicians and patients by providing enhanced ability of a physician to visualize a biopsy needle to obtain a sample of material from a target site without requiring an open incision or use of large-bore needles and/or laparoscopic trocars.

Current FNA techniques typically obtain only a small number of cells useful for diagnostic evaluation. As a result, this technique includes a risk of false negatives where the few cells obtained in a sample do not accurately represent the presence of a tumor or other disease condition. The small sample size may also limit the diagnostic value of the procedure if the cells obtained are sufficiently few in number or sufficiently damaged during collection that they do not enable a definitive diagnosis. Accordingly it would be advantageous to provide a needle useful for EUS and/or percutaneous FNB (fine needle biopsy) that can obtain a larger sample size (e.g., a larger number of cells in the sample or a "core" comprising intact adjacent cells held together in similar form to their native location, suitable for histological analysis) without requiring a larger-gauge needle or requiring multiple passes of the needle to reliably obtain a diagnostically efficacious sample with regard to the number and integrity of the cells in the sample. It would also be advantageous for the needle to be constructed in a manner providing for efficient operation through an endoscope such as a side-viewing gastric endoscope (also known as a duodenoscope), including ready navigation through the curvature(s) commonly required in using such an endoscope with a minimum of time and manipulation required.

BRIEF SUMMARY

Embodiments of needles disclosed here address these problems of the current technology and present advantages over existing needles with regard to both structure and methods. In one aspect a tissue-sampling needle device may include an elongate tubular cannula with a cannula wall defining a cannula lumen, where the cannula lumen extends longitudinally through the cannula. The cannula may include a distal beveled end with a long side and a short side and a notch through the cannula wall that is open to the cannula lumen. The notch is disposed proximally adjacent to the beveled distal cannula end and is generally centered in longitudinal alignment with the long beveled end side and opposite the short beveled end side. Also, the notch may include a distal lip defined by a portion of the cannula wall, the distal lip being configured to extend proximally from a distal-most end of the notch such that a central distal lip portion is disposed proximal of lip end portions that are continuous with generally longitudinal lateral sides of the notch, and to include a proximal-facing cutting edge.

In another aspect, a notched aspiration biopsy needle disclosed herein may include a flexible elongate tubular cannula, preferably sized no larger than 19-gauge, with a cannula wall defining a cannula lumen configured to communicate with a proximal source of suction. The cannula lumen extends longitudinally through the cannula, a distal beveled end of the cannula including a long side and a short side, and the structure includes a notch through the cannula wall, open to the cannula lumen. The notch is disposed proximally adjacent to the beveled distal cannula end and is generally centered in longitudinal alignment with the long beveled end side and opposite the short beveled end side, and the notch includes a cutting edge defined by a distal-facing portion of the cannula wall. A delivery sheath may also be included, where the delivery sheath is constructed including a coiled coated-wire tubular sheath body with an outer polymer coating. The coiled coated-wire tubular sheath body may include a stainless steel wire coated with PTFE or another lubricious polymer where the coated wire is coiled to form a generally patent tubular body. The sheath body may further be coated along its outer surface with an extruded polymeric overcoating such as nylon. A distalmost length of the polymeric overcoating may be provided at a greater thickness than a proximal length of the polymeric overcoating such that a distal sheath length has a larger outer diameter and greater columnar strength than a more proximal sheath length.

BRIEF DESCRIPTION OF THE DRAWINGS

In order to assist the understanding of embodiments of the invention, reference will now be made to the appended drawings, which are not necessarily drawn to scale or proportion, and in which like reference numerals generally refer to like elements. The drawings are exemplary only, and should not be construed as limiting the invention.

FIGS. 2A-2D show different views of a tissue-sampling needle device embodiment.

DETAILED DESCRIPTION

As used herein, the term "proximal" refers to the handle-end of a device held by a user, and the term "distal" refers to the opposite end. The term "surgical visualization device" refers to endoscopes including CCD, ultrasound, fiber optic, and CMOS devices, as well as other devices used for visualizing an internal portion of a patient body such as, for example, a laparoscope or bronchoscope.

Figure 1:
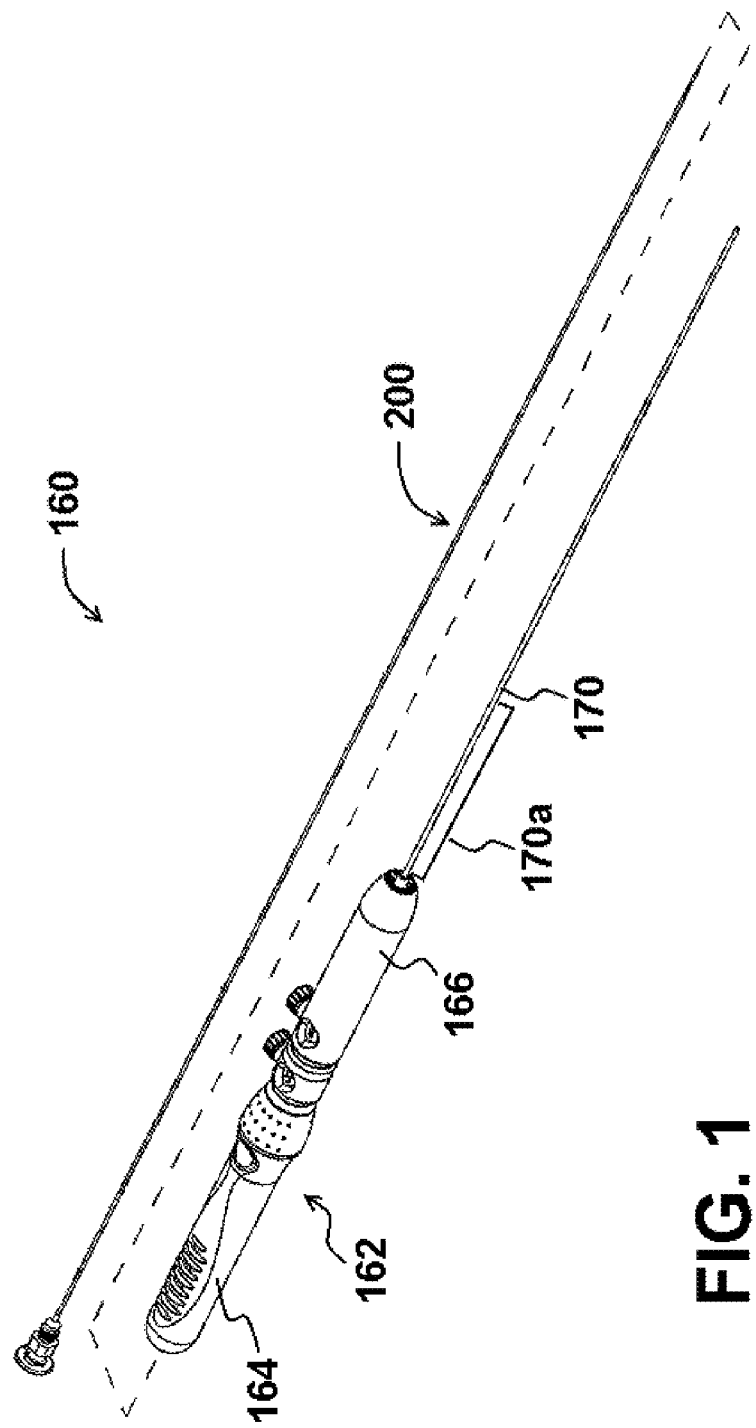
FIG. 1 shows an embodiment of a biopsy needle assembly.

One embodiment of a tissue-sampling needle device is described with reference to FIG. 1, which shows a biopsy needle assembly 160. The biopsy needle assembly 160 includes a handle 162, from which a sheath 170 extends distally. A needle device 200 is configured to be slidably disposed longitudinally through the sheath 170 and is shown and discussed below in greater detail with reference to FIGS. 2A-2D and FIG. 3. The structure of one embodiment of the sheath 170 is discussed in greater detail with reference to FIG. 3. In the embodiment of FIG. 1, the handle 162 includes a needle-moving element 164 and a sheath-moving element 166 and lockable stops with numerical indicia for user-controlled manipulation with respect to specified distances of longitudinal movement of each. In certain embodiments, the handle may be configured in a manner disclosed in U.S. Pat. No. 6,976,955 to Hardin, et al., which is incorporated herein by reference.

Detailed views of an embodiment of the needle portion of the biopsy needle assembly 160 are depicted in FIGS. 2A-2D, which show a tissue-sampling needle device 200 (which includes the needle cannula and stylet). As shown in the side plan view of FIG. 2A, the device includes a proximal handle or hub 202 from which an elongate tubular cannula 204 extends distally. In certain preferred embodiments, the hub 202 will be mounted or otherwise incorporated into a handle such as the handle 162 shown in FIG. 1. The cannula 204 includes a cannula wall 206 that defines a cannula lumen 208. A distal end 210 of the cannula 204 is lancet-beveled, including a long side 210a substantially parallel with the central longitudinal axis of the cannula 204 and extending to its distal-most tip end. A short side 210b of the beveled distal end 210 is opposite the long end 210a. A detailed illustration of the distal end 210 is shown in the top plan view of FIG. 2B, which (like FIGS. 2C-2D) shows only a distal end length of the device 200 shown in FIG. 2A. Other embodiments may include a double bevel, where one beveled surface is opposite the notch, or single or double bevels that are at least partially transverse relative to the notch 220.

As shown in the side plan view of FIGS. 2A and 2C, and in the perspective view of FIG. 2D, a notch 220 is disposed proximally adjacent to the beveled distal cannula end 210 and is generally centered in longitudinal alignment with the long beveled end side 210a and opposite the short beveled end side 210b. In preferred embodiments, the notch 220 is generally arcuate, defined on its distal side by a parabolic edge 222 extending along generally longitudinal, but somewhat curved lateral notch sides 224. The proximal edge 224 of the notch 220 preferably is formed as generally parabolic lip that joins the distal edge 222 at a pair of lip end portions 226 that preferably provide a curved transition between the distal lateral and proximal edges 222, 224. The radiused lip end portions 226 preferably are configured to provide stress relief within the cannula structure. A central proximal lip portion 225 of the proximal edge 224 preferably forms a distal-facing cutting edge. In preferred embodiments, the notch will occupy less than about one-half the circumference of the cannula 204 at the broadest point of the notch. Inclusion of the bevel illustrated in FIG. 2C may provide advantages for successful sample collection. Specifically, contact of the bevel face against tissue may create a slight bias/pressure toward the notch that will help tissue to be pulled/captured into the notch when the stylet (described below) is withdrawn, including that contact pressure on the notch side of the shaft surface may be slightly greater than on the exterior surface immediately opposite the notch. The cannula 204 has a consistent or at least substantially consistent outer diameter along at least its distal length from distal of the notch 220, across the notch, and proximal of the notch.

An elongate stylet 230 may be disposed removably through the cannula lumen 208. In preferred embodiments the stylet 230 will occupy substantially or nearly an entire cross-sectional area of at least a lengthwise portion of the cannula lumen 208. And, as shown in FIG. 2C, a distal end 232 of the stylet 230 may be rounded and dimensioned not to extend out of the distal beveled cannula end 210. This construction will provide enhanced support for the cannula (particularly during navigation to a target site). It should be appreciated that a beveled stylet end or other stylet end configuration may be practiced within the scope of the present invention and, in the case of a beveled-end stylet, may provide a generally solid cutting and/or tissue-penetrating distal tip end formed by matching bevels of the stylet 230 and cannula 204. A proximal-end stylet cap 234 attached to the stylet 230 is shown with a protruding tab 235 configured to align with the short side 210b of the beveled distal cannula end 210. In a needle assembly like the needle assembly 160 of FIG. 1, this feature may lock into a corresponding notch on the handle 162 and be used by treating personnel to determine the rotational orientation of the distal needle end region including the notch 220 and distal bevel.

The needle embodiment is shown here with an open distal end, but, in certain embodiments, the distal beveled needle end may be closed, such that the lumen 208 extending longitudinally through the cannula terminates within the cannula 204. In these embodiments, a stylet may be reinserted into the needle lumen after the sample has been excised and captured through the notch into the needle lumen. In such a circumstance, the stylet may be extended distally to cover the open notch (thereby preventing contamination of the sample by inadvertent collection of cells along the needle track during withdrawal of the needle), but leaving room in a closed needle lumen portion for the sample to remain intact between the notch and a closed distal end in an embodiment where the needle lumen is closed at the distal end.

In one exemplary embodiment of the needle portion of the biopsy needle assembly, the cannula 204 may be constructed as a 20-gauge needle made of 304 stainless steel, with an inner diameter of about 0.9 mm (about 0.03 inches) and an outer diameter of about 0.91 mm (about 0.036 inches). In this embodiment, the notch 220 may be circumferentially located opposite and proximal of a distal bevel that is at about a 18.3° angle (±about 5°) relative to the short side such that a proximal-most end of the notch 220 (defined by the curved lip end portion 226) is about 7.1 mm (about 0.28 inches) longitudinally proximal of the distal-most tip end of the cannula 204. In this embodiment, the longitudinal distance between the distal-most notch edge 222 and the distal-most portion of the rounded proximal cutting lip 225 will be about 3 mm (about 0.12 inches). The distal-most portion of the proximal lip 225 will be about 0.56 mm (about 0.022 inches) from the proximal-most end of the notch 220, which will be defined by a curved lip end portion 226, including a radius of curvature of about 0.05 mm (0.002 inches), joining the proximal edge 224 with the distal edge 222. A beveled or round-tipped NiTi stylet 230 may be disposed slidably/removably through the cannula lumen. It should be appreciated that, while a needle not larger than a 19-gauge needle is preferred, smaller gauge needles such as—for example—22-gauge and 25-gauge needles may be practiced within the scope of the present disclosure (although, it will be appreciated that their absolute dimensions will vary from those disclosed for the 20-gauge example). The notch may be oriented with a proximal-facing cutting lip (e.g., such as is disclosed in co-owned U.S. Pat. Publ. 2012/0253228 to Schembre et al., which is incorporated herein by reference in its entirety).

As shown in FIG. 2A, some embodiments of the cannula 204 may include surface features 240 configured to enhance echogenicity, thereby providing an improved ability to navigate the device during an EUS procedure. The surface features 240 are shown here as dimples on an exterior surface of the cannula 204, but may alternatively be embodied as grooves or other regular or irregular features on an external or internal surface. Embedded echogenic features such as bubbles, voids, or pieces of echo-contrasting materials may also be used within the scope of the present invention. Those of skill in the art will appreciate that many currently-known and/or future-developed echogenicity-enhancing means may be used within the scope of the present invention. As used herein, the terms echogenic and echogenicity-enhancing are used to refer to structural features that increase the reflectivity of ultrasound waves used during ultrasound visualization of a device, with the increase being over the typical ultrasound reflectivity/visualizability of a device lacking the features described.

The echogenic features 240 may extend distally across the cannula surface radially opposite space occupied by the notch 220. It is preferable that echogenicity-enhancing features be disposed at a specified predetermined distance from the distal-most tip end of the cannula 204. Although the echogenic features 240 are shown at a distance from the notch 220, a cannula according to the present embodiments may be constructed with those echogenic features disposed flush up to the margins of the notch. The stylet 230 may include echogenicity-enhancing features instead of or in addition to those that may be disposed on the cannula 204.

Figure 3:
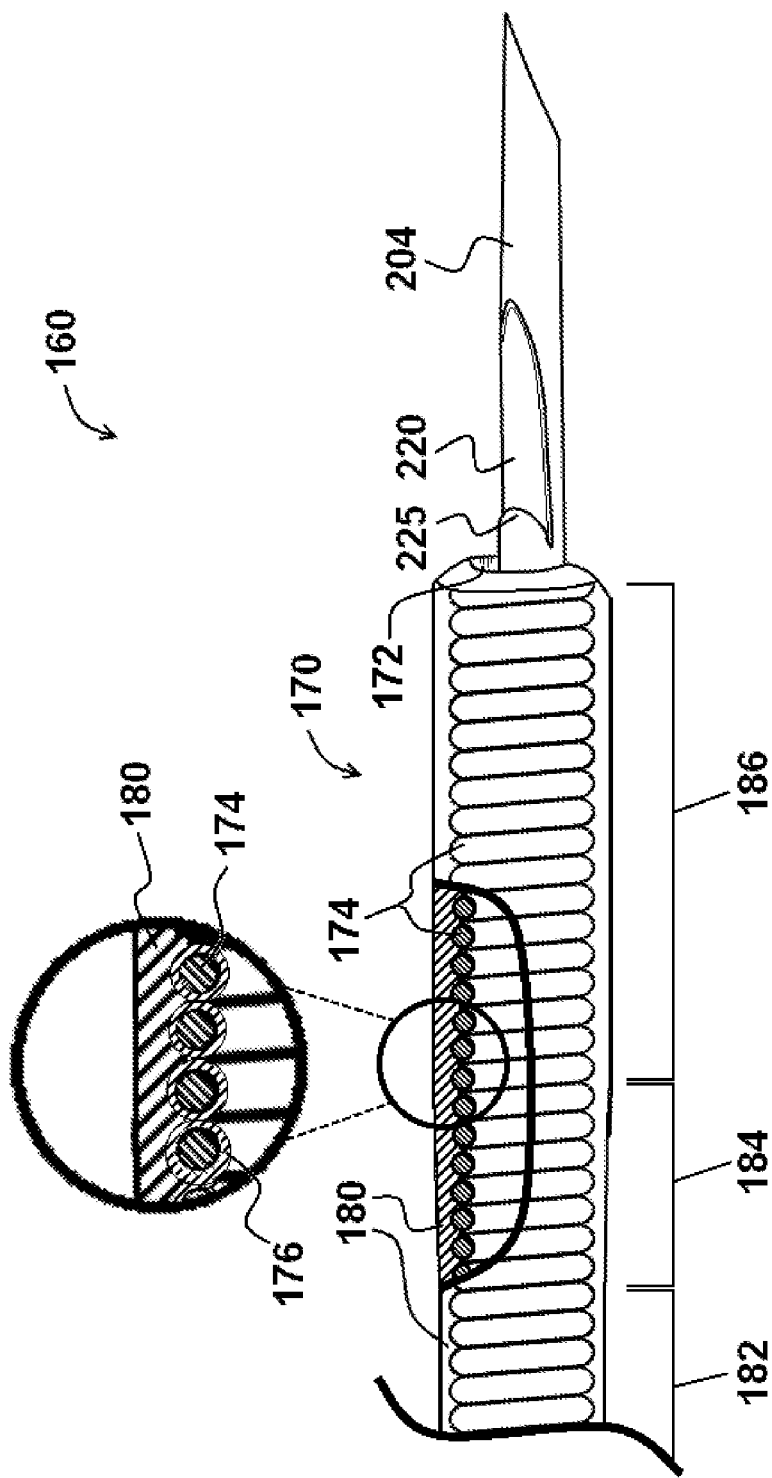
FIG. 3 shows a distal portion of the biopsy needle assembly of FIG. 1 with the needle extended from the sheath, and the sheath partially shown in longitudinal section.

FIG. 3 shows a distal portion of the biopsy needle assembly of FIG. 1 with the needle 204 extended from the sheath, and the sheath 170 partially shown in longitudinal section. A call-out/detail portion shows the longitudinal cross-sectional view in greater/magnified detail. The sheath 170 may be constructed as including a coiled coated-wire tube defining a longitudinal sheath lumen 172. The needle cannula 204 is slidably disposed through the sheath lumen 172, and the sheath 170 is fixed to a portion of the handle 162. At least a distal length of the sheath 170 extending from a distal sheath end will include the coiled coated-wire tube construction, and the entire sheath may be so constructed. In one embodiment, the coiled coated-wire tube construction includes stainless steel wire 174 (such as, for example, 304 stainless steel) that is coated with a lubricious polymer 176 (such as, for example, PTFE, whether alone or in combination with other material(s)) and coiled to form a wire tube of substantially consistent inner and outer diameter. This construction will provide desirable columnar support and protection for the needle cannula 204 and for the interior surface of an endoscope working channel through which the device is to be operated.

In some embodiments, the sheath 170 may also include a polymeric overcoating 180 (illustrated as a substantially transparent overcoating in FIG. 3). In one desirable embodiment, nylon is extruded over the tube body. One desirable nylon polymer is commercially available as AESNO MED™ from Arkema of King of Prussia, Pa. The overcoating 180 will provide additional strength and integrity for the tube body. The distal end of the device 100 may be subjected to rather severe curvature(s) when directed through an endoscope working channel to a target site. Such severe curvature exerts forces on the needle cannula 204 that theoretically could increase a risk of undesirable bending and/or kinking, particularly in the region of the notch 220, and it would be desirable to avoid any such deformation of the cannula.

In one example, a surgical visualization device such as an endoscopic ultrasound (EUS) duodenoscope may be used to identify a target area for biopsy in or near the pancreas head of a patient. The curvature typically required by the scope to visualize this region is so tight as not to allow passage through the scope's working channel of a biopsy needle (either absolutely, or without risking damage to the needle). In such cases, the scope is typically used to identify the region via EUS, including positional maneuvering to get the distal end of the working channel in place to access the target, whereupon the scope must be relaxed at least somewhat to allow the biopsy needle to be directed slight out of the working channel. Thereafter, the target must be re-acquired before the biopsy needle can be used for collection therefrom. The presently disclosed system advantageously provides a novel sheath with sufficient flexibility and needle-support that the intermediate relaxation/re-targeting step is not needed, and the cannula 204, including the notch 220 have columnar support sufficient to minimize the likelihood of undesired deformation.

The polymeric overcoating 180 will limit "gapping" between adjacent coils of the sheath's tube body during manipulation, including torquing, curving, etc. When the notch 220 is within the sheath lumen, this will help prevent the lip 225 from catching on a coil or gap between adjacent coils. It will also limit—but not unduly—the curvature of the sheath. In one preferred embodiment, shown in FIG. 3, the polymeric overcoating 180 includes a thicker extruded portion 186 along a distalmost length of the sheath 170. As shown in FIG. 3, a proximal length 182 includes a thinner overcoating that ramps along a smooth, non-stepped transition length 184 to a larger outer diameter distal length 186, where the distal face/terminus of the sheath may be rounded/polished to present a surface that is smoothly navigable through a working channel of a surgical visualization device. Those of skill in the art will appreciate, with reference to the present teaching, that this structure provides for increased columnar strength of the sheath along a distalmost length that overlies the needle notch 220. This thicker/larger outer diameter length may extend about 10 mm to about 50 mm or more from the distal sheath end. In addition to increased columnar strength, this larger-OD length 186 will limit the amount by which a scope elevator can bend/torque the sheath 170, which will further protect the integrity and functionality of the needle body 204. In other words, the larger outer diameter distal sheath length preferably is effective to limit endoscope elevator deflection of the sheath to less than the degree of deflection allowed by the smaller outer diameter distal sheath length. The larger-OD distal length may extend about 5% to about 30% of the sheath length from its distal end. That thicker-OD distal length may be about 5% to about 20%, and preferably about 9% to about 17%, larger in diameter than the thinner-OD proximal length of sheath overcoating.

In a sheath embodiment configured for use with the illustrative example of a 20-gauge needle described above, the coiled coated-wire tube construction exclusive of the overcoating 180 may have an outer diameter of about 2.18 mm (about 0.086 inches). The overcoated outer diameter may be about 2.2 mm (about 0.09 inches) along the proximal/smaller diameter length and about 2.5 mm (about 0.1 inches) along the distal/larger diameter length. The inner diameter, preferably effectively lined by the lubricious coating 176 of the wire 174, may be about 1.3 mm (about 0.05 inches).

At the same time, the construction disclosed here provides superior flexibility over other known sheath designs (e.g., PEEK sheaths) to provide the desired ease of access without scope re-positioning. This structural and functional advantage will help reduce procedure time, and will enhance the functional efficiency of endoscopic biopsy configured to obtain histological samples. In a typical deployment, the distal needle end will be nearly aligned with, or will be just proximal of the distal sheath end, which will provide the benefits described here during use.

Those of skill in the art will appreciate with reference to the present disclosure by way of further teaching in addition to the state of the art that a method of tissue collection may be implemented using the assembly 160 described above. The needle cannula 204, with the stylet 230 disposed therein, may directed via the working channel of a surgical visualization device (e.g., an EUS duodenoscope) into a target site to be sampled (e.g., a suspected tumor mass in the head of a patient's pancreas). The stylet 230 may be withdrawn and suction applied to the needle cannula lumen 208. One or more of suction, rotary manipulation, and/or longitudinal manipulation of the needle cannula 204 will excise (e.g., via the cutting lip 224) and capture tissue, which preferably will include sufficiently intact samples for histology, from the target site through the notch 220 into the lumen 208.

The sample obtained preferably will include a desirable number of intact cells, preferably more intact cells than are ordinarily obtained using a non-notched FNA biopsy needle ("more" indicating both a greater number and a higher degree of tissue/cell integrity within the sample obtained). It has been found that histological-grade FNB samples may be obtained in this manner, which may be preferred for certain diagnostic purposes over the cytological-grade samples typically obtained through FNA. The needle may then be withdrawn from the patient's body.

In one preferred embodiment, during introduction of the device into a patient body, the cannula 204 will be directed through the working channel of a peroral endoscope such as a duodenoscope into a patient's body. It is then navigated (under ultrasound visualization if echogenicity-enhancing features are provided, as in the embodiment shown in FIGS. 1-3) into a target site. In other embodiments, the device may be introduced through other access means known in the art including percutaneous means such as direct insertion of the needle cannula through a patient's skin or insertion through a trocar, sheath, or other access device (with or without endoscopic or ultrasound visualization), all within the scope of the present invention. It should also be appreciated that an outer sheath may be disposed slidably along the exterior of the cannula 204 and the needle retracted thereinto (and/or the sheath distally advanced) so that the sheath is disposed over the notch 220 after the sample is collected. This configuration, which may be practiced within the scope of the present invention, may lessen the likelihood that the sample collected will become lost or contaminated during needle withdrawal.

The needle device and methods disclosed here provide the advantages associated with FNA needles of small size and maneuverability, while offering a means of collecting more intact samples from target sites. They also are not hampered by the guillotine-style moving parts of other notched needle systems known in the biopsy art (which are generally larger in scale due to a need for having a cutting member that movably transects the notch).

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention. In the event of any inconsistent disclosure or definition from the present application conflicting with any document incorporated by reference, the disclosure or definition herein shall be deemed to prevail.

The invention claimed is:

1. A biopsy needle assembly configured to collect histological samples via a surgical visualization device, the assembly comprising:
    an elongate notched needle cannula including a distal notch open through the elongate notched needle cannula to a longitudinal needle lumen, which longitudinal needle lumen extends through the elongate notched needle cannula; and
    an elongate sheath;
    where the elongate sheath comprises a longitudinal sheath lumen through which the elongate notched needle cannula is slidably disposed;
    where the elongate sheath includes a generally cylindrical body defining the longitudinal sheath lumen, the generally cylindrical body including:
        a coiled coated-wire tube extending proximally from a distal body end, wherein the coiled coated-wire tube includes a plurality of adjacent coils;
        a sheath overcoating around the coiled coated-wire tube; and
    where the coiled coated-wire tube has a substantially consistent outer diameter along an entire length of the coiled coated-wire tube, the elongate notched needle cannula has a substantially consistent outer diameter along an entire length of the elongate notched needle cannula, and the sheath overcoating includes a first thickness along a distal sheath length, the sheath overcoating includes a second thickness along a proximal sheath length, and where the first thickness is greater than the second thickness such that the first thickness causes an outer diameter of the distal sheath length to be larger than an outer diameter of the proximal sheath length, wherein the sheath overcoating is in contact with and extends contiguously between the plurality of adjacent coils along the distal sheath length and along the proximal sheath length.

2. The assembly of claim 1, where the sheath overcoating comprises nylon.

3. The assembly of claim 1, where the outer diameter of the distal sheath length is about 5% to about 20% greater than the outer diameter of the proximal sheath length.

4. The assembly of claim 1, where a wire that forms the coiled coated-wire tube is coated with PTFE or another lubricious polymer.

5. The assembly of claim 1, where the elongate notched needle cannula includes a beveled distal end tip, and the distal notch is located radially opposite and longitudinally proximal of the beveled distal end tip.

6. The assembly of claim 1, wherein the distal notch is aligned within the distal sheath length when a distal end tip of the elongate notched needle cannula is aligned with or near a distal sheath end.

7. The assembly of claim 1, where the outer diameter of the distal sheath length is effective to limit endoscope elevator deflection of the elongate sheath to less than deflection allowed by the outer diameter of the proximal sheath length.

8. The assembly of claim 1, where the distal sheath length extends about 10 mm to about 50 mm from a distal sheath end.

9. The assembly of claim 1, further comprising a stylet removably disposed through the longitudinal needle lumen.

10. The assembly of claim 1, where the elongate sheath comprises stainless steel wire coated with PTFE and wound to form a consistent-diameter tube.

11. The assembly of claim 1, where the sheath overcoating includes extruded nylon continuously forming the outer diameter f the distal sheath length, the outer diameter proximal sheath length, and a smooth, non-stepped transition therebetween.

12. The assembly of claim 1, where the sheath overcoating is effective to limit gapping between adjacent coils of the coiled coated-wire tube during manipulation of the coiled coated-wire tube.

13. The assembly of claim 1, wherein the elongate notched needle cannula includes a consistent outer diameter along at least a distal length of the elongate notched needle cannula from distal of the distal notch, across the distal notch, and proximal of the distal notch.

14. The assembly of claim 1, wherein the elongate notched needle cannula includes a pattern of echogenic surface features disposed immediately adjacent to and proximal of the distal notch.

15. The assembly of claim 1, wherein the elongate notched needle cannula is configured as a 20-gauge needle including an echogenically dimpled surface adjacent the distal notch.

16. The assembly of claim 15, where the coiled coated-wire tube of the elongate sheath comprises PTFE-coated stainless steel wire and the sheath overcoating comprises nylon.

17. A notched aspiration biopsy needle device, comprising:
a flexible elongate tubular cannula sized no larger than 19-gauge, including a cannula wall defining a cannula lumen, which cannula lumen is configured to communicate with a proximal source of suction;
wherein the cannula lumen extends longitudinally through the flexible elongate tubular cannula;
a distal beveled end of the flexible elongate tubular cannula including a long side and a short side;
a notch through the cannula wall, the notch being open to the cannula lumen;
wherein the notch is disposed proximally adjacent to the distal beveled end and is generally centered in longitudinal alignment with the long side of the distal beveled end and opposite the short side of the distal beveled end;
wherein the notch includes an arcuate cutting edge defined by a distal-facing portion of the cannula wall which distal-facing portion of the cannula wall
is within the circumference of the cannula wall, and extends into the notch; and
an elongate sheath;
where the elongate sheath comprises a longitudinal sheath lumen through which the flexible elongate tubular cannula is slidably disposed;
where the sheath includes a generally cylindrical body defining the longitudinal sheath lumen, the generally cylindrical body including:
a coiled coated-wire tube extending proximally from a distal body end, wherein the coiled coated-wire tube includes a plurality of adjacent coils;
a sheath overcoating around the coiled coated-wire tube; and
where the coiled coated-wire tube has a substantially consistent outer diameter along an entire length of the coiled coated-wire tube, the flexible elongate tubular cannula has a substantially consistent outer diameter along an entire length of the flexible elongate tubular cannula, and the sheath overcoating includes a first thickness along a distal sheath length, the sheath overcoating includes a second thickness along a proximal sheath length, and where the first thickness is greater than the second thickness such that the first thickness causes an outer diameter of the distal sheath length to be larger than an outer diameter of the proximal sheath length, wherein the sheath overcoating is in contact with and extends contiguously between the plurality of adjacent coils along the distal sheath length and along the proximal sheath length.

18. The needle device of claim 17, further comprising a stylet disposed through, and occupying substantially an entire cross-sectional area of, at least a lengthwise portion of the cannula lumen, wherein a distal end of the stylet is configured not to extend beyond the distal beveled end of the flexible elongate tubular cannula.

19. The needle device of claim 17, wherein the flexible elongate tubular cannula is configured as sufficiently long and flexible for passage through a working channel of a peroral surgical visualization device to a target site within a patient abdomen.

20. The needle device of claim 17, further comprising a pattern of echogenic surface features disposed immediately adjacent to and proximal of the notch.

\* \* \* \* \*